United States Patent
Higashi et al.

(10) Patent No.: US 8,779,762 B2
(45) Date of Patent: Jul. 15, 2014

(54) INSPECTION DEVICE

(75) Inventors: Masayoshi Higashi, Tokyo (JP);
Masaaki Kurokawa, Tokyo (JP);
Kayoko Kawata, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 138 days.

(21) Appl. No.: 13/386,538

(22) PCT Filed: Sep. 2, 2010

(86) PCT No.: PCT/JP2010/065027
§ 371 (c)(1),
(2), (4) Date: Jan. 23, 2012

(87) PCT Pub. No.: WO2011/074294
PCT Pub. Date: Jun. 23, 2011

(65) Prior Publication Data
US 2012/0119733 A1  May 17, 2012

(30) Foreign Application Priority Data
Dec. 18, 2009 (JP) .................. 2009-287612

(51) Int. Cl.
*G01N 27/82* (2006.01)
(52) U.S. Cl.
USPC .................................................. 324/240
(58) Field of Classification Search
USPC .................................................. 324/240
See application file for complete search history.

(56) References Cited

U.S. PATENT DOCUMENTS

| 4,337,431 | A | 6/1982 | Hale |
| 4,625,165 | A | 11/1986 | Rothstein |
| 4,876,506 | A | 10/1989 | Brown et al. |
| 4,992,735 | A | 2/1991 | Cullen et al. |
| 5,388,129 | A | 2/1995 | Hartley |
| 5,402,066 | A | 3/1995 | Hickman, Jr. et al. |
| 6,608,478 | B1 * | 8/2003 | Dziech et al. ............ 324/262 |

FOREIGN PATENT DOCUMENTS

| DE | 84 35 914 U1 | 5/1985 |
| EP | 0 411 874 A2 | 2/1991 |
| JP | 61-132856 A | 6/1986 |
| JP | 63-065361 A | 3/1988 |

(Continued)

OTHER PUBLICATIONS

Abstract of JP 61-132856, Jun. 20, 1986.*

(Continued)

*Primary Examiner* — Bot Ledynh
(74) *Attorney, Agent, or Firm* — Westerman, Hattori, Daniels & Adrian, LLP (57) ABSTRACT

An inspection device that is capable of inspecting all heat-transfer-tube sealing portions in a steam generator and that is also capable of analyzing a defect shape is provided. An inspection device that employs the eddy-current flaw detection method to inspect the presence/absence of a defect in a welded portion (103) between a tube (101) and a tube plate (102) is provided with a main unit (41) that has a circular-column portion (41A), which is inserted into the tube (101), and a flange portion (41B), which is pressed against the tube plate (102), and that is rotatable with respect to the welded portion (103); a probe (42) that is disposed inside the main unit (41), that can be moved close to and away from the welded portion (103), and that detects a defect in the welded portion (103); and a pressing portion (44) that presses the probe (42) toward the welded portion.

10 Claims, 9 Drawing Sheets

(56) References Cited

FOREIGN PATENT DOCUMENTS

| | | |
|---|---|---|
| JP | 63-70077 U | 5/1988 |
| JP | 05-322855 A | 12/1993 |
| JP | 06-034607 A | 2/1994 |
| JP | 06-258295 A | 9/1994 |
| JP | 06-281628 A | 10/1994 |
| JP | 06-347448 A | 12/1994 |
| JP | 07-505468 A | 6/1995 |
| JP | 2000-275221 A | 10/2000 |
| JP | 2005-262218 A | 9/2005 |

OTHER PUBLICATIONS

Extended European Search Report dated Jun. 5, 2013, issued in corresponding European Patent Application No. 10837324.2.
Inrternational Search Report of PCT/JP2010/065027, mailing date Sep. 28, 2010.

* cited by examiner

INSPECTION DEVICE

TECHNICAL FIELD

The present invention relates to an inspection device that is suitably employed for inspecting a welded portion between a tube and a tube plate, in particular, a heat-transfer-tube sealing welded portion in a steam generator.

BACKGROUND ART

A steam generator (hereinafter, referred to as "SG") that generates steam by boiling secondary cooling fluid with the heat of primary cooling fluid is provided with a plurality of heat-transfer tubes and a tube plate to which ends of the heat-transfer tubes are welded, thereby supporting the heat-transfer tubes. The secondary cooling fluid outside the heat-transfer tubes is heated by the primary cooling fluid that flows inside the heat-transfer tubes. The tube plate not only supports the heat-transfer tubes but also constitutes a partition between the primary cooling fluid and the secondary cooling fluid.

Accordingly, welded portions (hereinafter, referred to as "heat-transfer-tube sealing portions") between the heat-transfer tubes and the tube plate are required to prevent leakage or the like of the primary cooling fluid to the secondary-cooling-fluid side.

In this case, if there is a defect in the heat-transfer-tube sealing portion, the defect may form an opening toward the primary-cooling-fluid side or the secondary-cooling-fluid side due to pressure, etc. from the primary cooling fluid, and a pathway (leakage pathway) through which the primary cooling fluid or the like leaks may be formed.

Therefore, in the final stage of SG manufacturing, integrity verification is performed in which an SG is subjected to a pressure-endurance test to confirm the presence/absence of leakage pathways. However, it is preferable that defects at the heat-transfer-tube sealing portions be detected in advance before performing such a test.

In the case in which such a defect is a crack that opens at a surface of the heat-transfer-tube sealing portion, the defect can be detected by a permeation test (PT) or a leakage test. However, there is a problem in that an internal defect such as a blowhole, that is, a defect which does not open at the surface, cannot be detected by such inspection methods.

On the other hand, a radiation test (RT) can also detect internal defects in the heat-transfer-tube sealing portions. With the RT, however, the defect inspection speed is lower than in the above-described inspection methods. Accordingly, inspecting all of heat-transfer-tube sealing portions in an SG having a few thousand heat-transfer tubes with RT is exceedingly time consuming, and thus, it is not practical.

Although a blowhole can be detected by RT inspection, there is a problem in that the depth (distance from the surface to the blowhole) of the blowhole cannot be determined.

Accordingly, it is desirable to apply the eddy-current flaw detection method (ECT) with which relatively rapid inspection can be performed for defects at the surfaces of the heat-transfer-tube sealing portions, and various inspection methods have been proposed (for example, see Patent Literatures 1 and 2).

CITATION LIST

Patent Literature

{PTL 1} Japanese Unexamined Patent Application, Publication No. Hei 5-322855.

{PTL 2} Japanese Unexamined Patent Application, Publication No. 2005-262218.

SUMMARY OF INVENTION

Technical Problem

ECT is a method in which a high-frequency eddy current is made to flow at a surface of an inspection target, such as the heat-transfer-tube sealing portion, etc., with an ECT coil, and impediment to the flow of the eddy current and phase changes thereof due to a defect are detected as changes in electromagnetic induction. Meanwhile, fluctuations in distance between the coil and the inspection target are also detected.

Accordingly, in order to accurately detect the defect, it is necessary to maintain a constant gap between the ECT coil and the surface of the heat-transfer-tube sealing portion. In other words, there is a problem in that the ECT coil needs to be moved so as to follow asperities at the surface of the heat-transfer-tube sealing portion.

Furthermore, the area that can be inspected at one time for the presence/absence of a defect with ECT is substantially the same area as the area of the ECT coil. Accordingly, there is a problem in that the ECT coil needs to be moved in the circumferential direction and the radial direction of a heat-transfer-tube sealing portion in order to perform inspection for the presence/absence of a defect in the heat-transfer-tube sealing portion.

The present invention has been conceived to solve the above-described problems, and an object thereof is to provide an inspection device that is capable of inspecting all of heat-transfer-tube sealing portions in a steam generator and that is also capable of analyzing a defect shape.

Solution to Problem

The present invention provides the following solutions in order to achieve the above-described object.

An inspection device according to an aspect of the present invention is an inspection device that employs an eddy-current flaw detection method to perform inspection for a presence or an absence of a defect in an welded portion between a tube and a tube plate, the inspection device including a main unit that has a circular-column portion, which is inserted into the tube, and a flange portion, which is pressed against the tube plate, and that is rotatable with respect to the welded portion; a probe that is disposed inside the main unit, that can be moved close to and away from the welded portion, and that detects a defect in the welded portion; and a pressing portion that presses the probe toward the welded portion.

With the above-described aspect of the present invention, the probe is pressed against the welded portion by inserting the main unit into the tube and by pressing the flange portion against the tube plate. By rotating the main unit with respect to the tube in this state, the probe can be moved in the circumferential direction at a surface of the welded portion, and the presence/absence of defects in the welded portion can be inspected. In other words, it is possible to stably perform inspection for the presence/absence of defects in predetermined areas in a plurality of welded portions, and inspection for the presence/absence of defects in the plurality of welded portions can be performed in a short period of time.

Furthermore, the rotation direction of the probe with respect to the tube may be only one direction, that is, one rotation direction or the other rotation direction, or the probe may be rotatable in both directions.

In the case in which the main unit can be rotated in both directions, by comparing the inspection results obtained from one rotation direction and the inspection results obtained from the other rotation direction, disturbance noise due to surface protrusions or the like can be removed from the inspection results.

In the above-described invention, it is desirable that the pressing portion be an elastic member and that the pressing portion be disposed at least a predetermined distance away from the probe.

With the above-described aspect of the present invention, the probe is pressed against the welded portion by the pressing portion, which is an elastic member (for example, a spring). Accordingly, as compared with the case in which the probe is pressed against the welded portion by other means, the probe can be more reliably pressed against the welded portion.

Furthermore, even if the pressing portion is formed of a material, such as a metal material, etc., that influences inspection for the presence/absence of defects in which the eddy-current flaw detection is employed, for example, a metal material, because the probe is disposed a predetermined distance away from the pressing portion, inspection can be accurately performed without influencing the detection of defects in the welded portion. If a non-magnetic material, such as stainless steel, etc., is employed as the metal material, an eddy-current is even less likely to be excited, and the influence on the defect detection can be suppressed.

In inspection for the presence/absence of defects by the probe, the predetermined distance in this case specifically refers to a distance at which an eddy current is not excited at the pressing portion pressed by the probe or a distance at which, even if the eddy current is excited at the pressing portion, signals output from the probe due to the eddy current are negligible levels.

It is generally desirable that the separation be by a distance that roughly corresponds to the size of the ECT coil that forms the probe.

In the above-described invention, it is desirable that the main unit be provided with a plurality of the probes and that the plurality of the probes be disposed in a circumferential direction of the main unit at equal intervals.

With the above-described aspect of the present invention, because the probes are pressed against the welded portion at positions separated at equal intervals in the circumferential direction, the center of the main unit is aligned with the center of the tube. Accordingly, the distances between the probes and the welded portion are easy to keep constant, and disturbance noise due to fluctuations in the distances is less likely to be included in the inspection results from the probes.

Although the number of probes may be any number so long as it is more than one, three is desirable from the viewpoint of stability of the main unit. In the case where three probes are employed, it is preferable that the placement interval of the probes be about 120°.

In the above-described invention, it is desirable that the main unit be provided with a plurality of the probes and that each of the plurality of the probes be pressed against the welded portion at a different radial position.

With the above-described aspect of the present invention, by fully rotating the main unit with respect to the tube, inspection for the presence/absence of defect in the welded portion can be performed for a greater area as compared with the case in which one probe is provided. Specifically, by sequentially arranging the plurality of the probes from outside to inside in the radial direction of the welded portion, a greater area in the welded portion can be inspected in a short period of time.

Furthermore, the plurality of the probes may be disposed so that inspection areas of the individual probes do not overlap, or they may be disposed so that a portion of a region inspected by one probe overlaps with a region inspected by an adjacent another probe.

In the case in which the plurality of the probes are disposed so that the overlap occurs, one defect can be detected by at least two probes, making it possible to remove disturbance noise from the detection results from the probes. Specifically, the probability that the plurality of the probes cause the disturbance noise to occur at the same position is low, and thus, in many cases, the disturbance noise appears in the detection result from one probe. On the other hand, the defect is detected at the same position by the plurality of the probes. Accordingly, the disturbance noise can easily be removed from the detection results from the probes.

In the above-described invention, it is desirable that the plurality of the probes sequentially perform inspection for the presence or the absence of a defect in the welded portion.

With the above-described aspect of the present invention, because inspection by other probes is not performed when the one probe is performing the inspection for the presence/absence of defects, it is possible to prevent the other probes from affecting the inspection result from the one probe. Furthermore, because inspection by the plurality of the probes is sequentially performed, for example, the inspection region at the welded portion can be inspected without a gap while the main unit fully rotates.

In the above-described invention, it is desirable that a surface of the probe that comes in contact with the welded portion be formed so as to match the shape of the welded portion with which the probe is made to come in contact.

With the above-described aspect of the present invention, even if misalignment occurs, in which the center axis of the main unit and the center axis of the tube are shifted, the probes easily move to the regions of the welded portion that have the same shapes as the surfaces that come in contact with the welded portion. In other words, the tracking performance is increased. As a result, the precision of the inspection results from the probes for the presence/absence of defects can be increased.

In the above-described invention, it is desirable that a distal end of the circular-column portion be provided with an aligning portion that comes in contact with an inner circumferential surface of the tube in a rotatable manner and that aligns the center of the main unit and the center of the tube.

With the above-described aspect of the present invention, because the center of the main unit is aligned with the center of the tube by the aligning portion, even though inspection for the presence/absence of defects in the welded portion is performed by rotating the main unit, fluctuations in the distances between the probes and the welded portion can be suppressed. As a result, the precision of the inspection result from the probes for the presence/absence of defects can be increased.

In the above-described invention, it is desirable to include a holding portion that is inserted into another tube other than the tube into which the circular-column portion is inserted and that comes in contact with an inner circumferential surface of the other tube.

With the above-described aspect of the present invention, the holding portion and the aligning portion are individually inserted into the tubes and come in contact with the inner circumferential surface thereof, thereby facilitating alignment of the center of the main unit and the center of the tube.

Furthermore, as compared with the case in which only the aligning portion and the main unit are inserted into the tube, because the holding portion is inserted into another tube, the inspection device is secured to the tubes and the tube plate with the aligning portion and the holding portion. Because of this, even though the main unit is rotated with respect to the tube, recoil therefrom does not cause the inspection device to change its orientation or to be moved. That is, even though the main unit and the probes are rotated, the occurrence of misalignment in the main unit can be prevented.

Advantageous Effects of Invention

With the inspection device of the present invention, probes that detect defects in a welded portion are disposed inside a main unit which is rotatable with respect to the welded portion so as to be movable toward and away from the welded portion, the probes are pressed toward the welded portion by pressing portions, and thereby, an advantage is afforded in that all heat-transfer-sealing portions in a steam generator can be inspected and that defect shapes can be also analyzed.

DESCRIPTION OF EMBODIMENTS

An inspection device according to an embodiment of the present invention will be described with reference to FIGS. 1 to 13.

Figure 1:
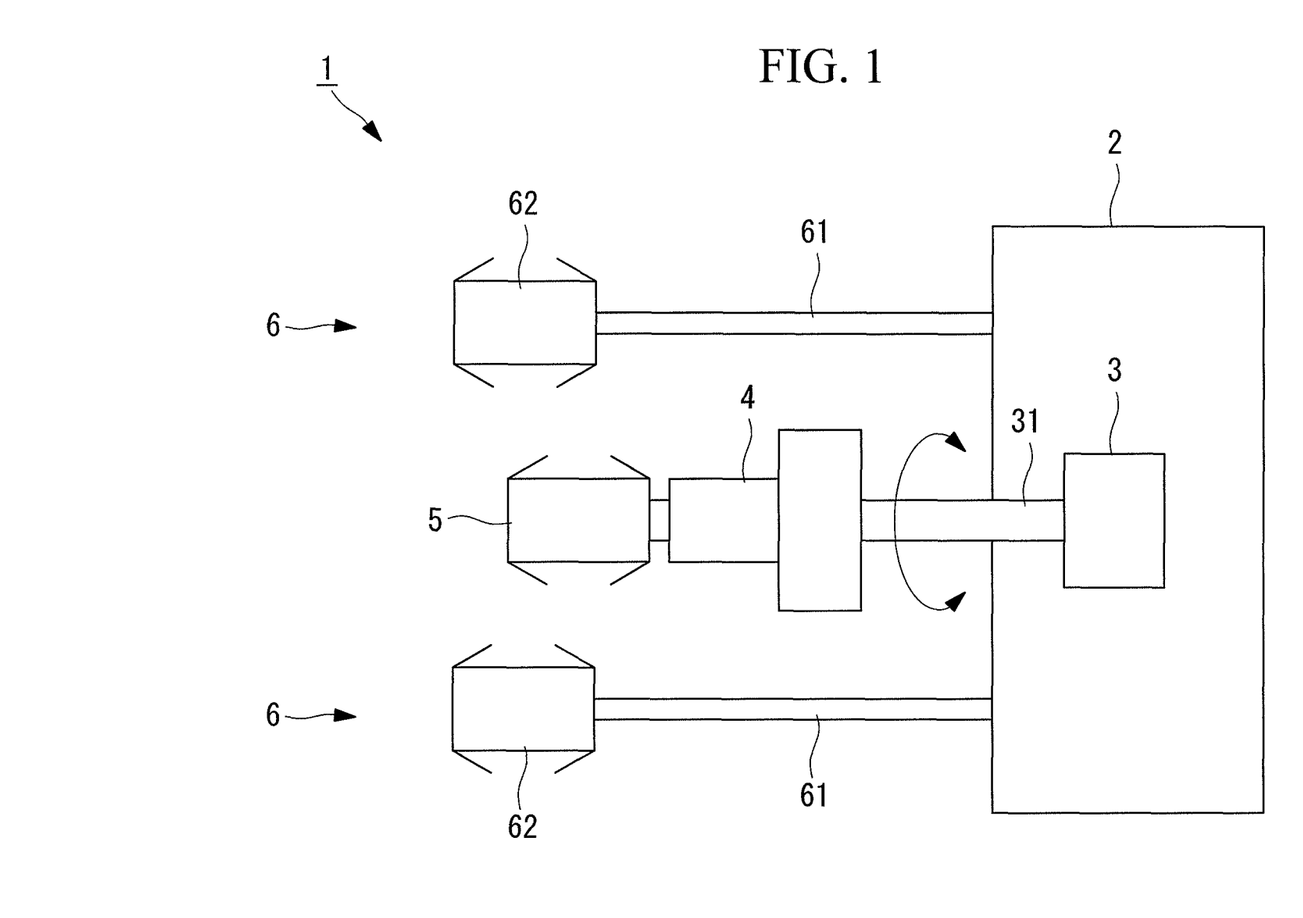
FIG. 1 is a schematic diagram for explaining the configuration of an inspection device according to an embodiment of the present invention.

FIG. 1 is a schematic diagram for explaining the configuration of the inspection device according to this embodiment.

In this embodiment, the inspection device of the present invention will be described as applied to an inspection device that employs the eddy-current flaw detection method to perform inspection for the presence/absence of a defect, such as a blowhole, etc., in heat-transfer-tube sealing portions (welded portions) 103, which are welded portions between heat-transfer tubes (tubes) 101 and a tube plate 102 in a steam generator.

As shown in FIG. 1, an inspection device 1 is mainly provided with a casing 2, a rotation motor 3, a probe portion 4, a probe stabilizer (aligning portion) 5, and securing portions 6.

As shown in FIG. 1, the casing 2 supports the probe portion 4, the probe stabilizer 5, and the securing portions 6, and internally accommodates the rotation motor 3.

The rotation motor 3 rotates the probe portion 4 in one rotation direction and the other rotation direction with respect to the heat-transfer-tube sealing portion 103.

The rotation motor 3 is disposed inside the casing 2 and is connected to the probe portion 4, which is disposed outside the casing 2, via a rotating shaft 31 that can be rotated about a center axis.

A known motor can be employed as the rotation motor 3; it is not particularly limited.

Figure 2:
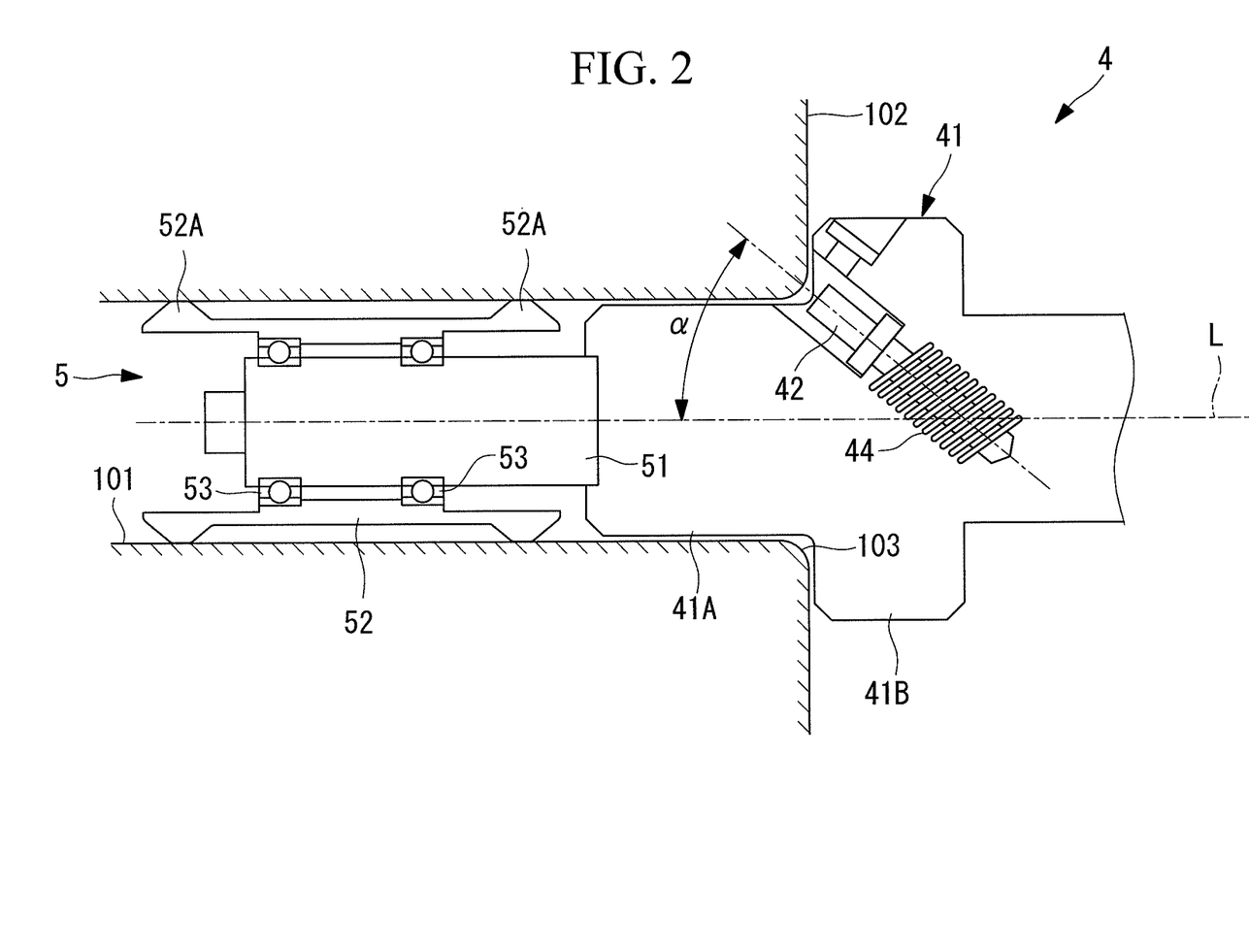
FIG. 2 is a sectional view for explaining the configurations of a probe main unit and a probe stabilizer in FIG. 1.
Figure 3:
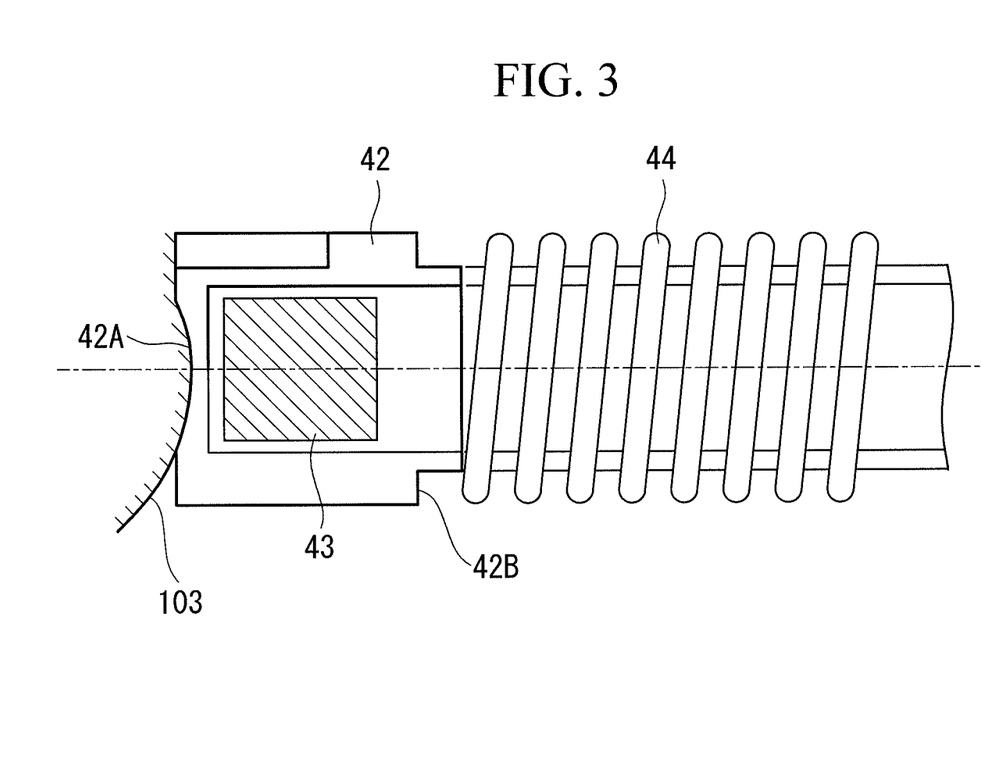
FIG. 3 is a sectional view for explaining the configurations of a sensor portion, an ECT coil, and a spring in FIG. 2.

FIG. 2 is a sectional view for explaining the configurations of a probe main unit and a probe stabilizer in FIG. 1. FIG. 3 is a sectional view for explaining the configurations of a sensor portion, an ECT coil, and a spring in FIG. 2.

The probe portion 4 detects the presence/absence of defects in the heat-transfer-tube sealing portion 103.

As shown in FIGS. 2 and 3, the probe portion 4 is mainly provided with a probe main unit (main unit) 41, sensor portions (probes) 42, ECT coils 43, and springs (pressing portions) 44.

The probe main unit 41 internally accommodates the sensor portions 42, the ECT coils 43, the springs 44, and so on, and places the ECT coils 43 close to the heat-transfer-tube sealing portion 103. Furthermore, in consideration of the influence on the detection of the presence/absence of defects by the ECT coils 43 with the eddy-current flaw detection method, the probe main unit 41 is formed of a material that is less likely to cause such an influence, such as plastic, etc. As shown in FIG. 2, the probe main unit 41 is mainly provided with a circular-column portion 41A and a flange portion 41B.

The circular-column portion 41A is a portion formed on a distal-end side (left side in FIG. 2) of the probe main unit 41 and is a portion formed with a diameter smaller than the inner diameter of the heat-transfer tube 101 so that it can be inserted into the heat-transfer tube 101. Furthermore, the probe stabilizer 5 is attached to the distal-end side of the circular-column portion 41A, and the flange portion 41B is provided at a casing side (right side in FIG. 2) of the circular-column portion 41A.

The flange portion 41B is a portion formed at the casing side of the probe main unit 41 and is a portion formed with a diameter larger than the inner diameter of the heat-transfer tube 101 so as to be pressed against the tube plate 102. Furthermore, the circular-column portion 41A is provided at the distal-end side of the flange portion 41B, and the rotating shaft 31 is attached to the side thereof closer to the casing 2.

Figure 4:
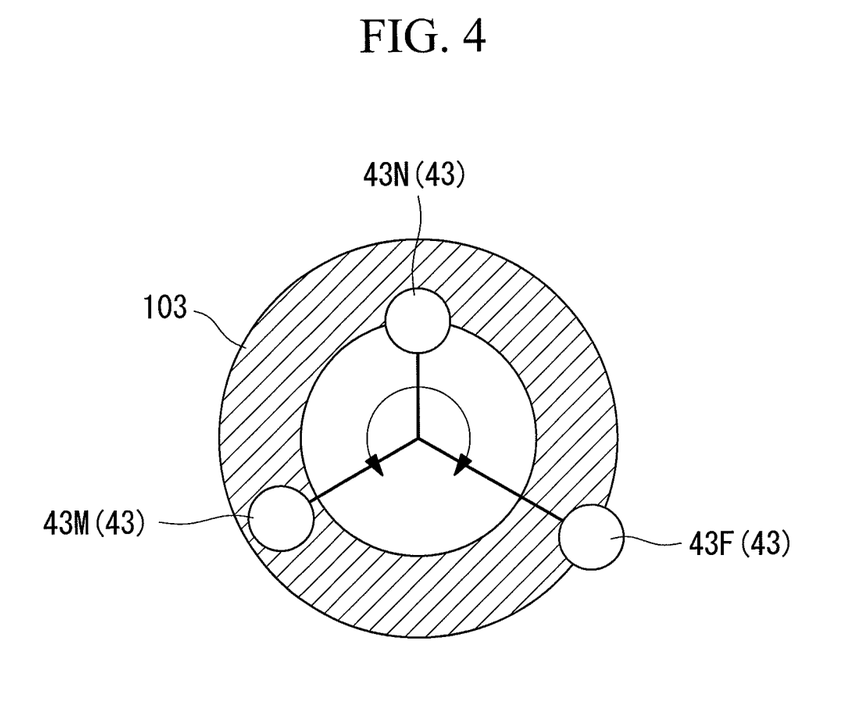
FIG. 4 is a schematic diagram for explaining the placement of the sensor portion in FIG. 2.

FIG. 4 is a schematic diagram for explaining the placement of the sensor portions in FIG. 2.

As shown in FIG. 2, the sensor portions 42, the ECT coils 43, and the springs 44 are disposed at a connecting portion between the circular-column portion 41A and the flange portion 41B of the probe main unit 41.

Furthermore, in this embodiment, three sets of the sensor portion 42, the ECT coil 43, and the spring 44 are disposed in the probe main unit 41. More specifically, as shown in FIG. 4 which is a diagram in which the probe main unit 41 is viewed from the casing 2, the three sets of the sensor portion 42, the ECT coil 43, and the spring 44 are individually disposed at about 120° intervals.

On the other hand, as shown in FIG. 4, the three sets of the sensor portion 42, the ECT coil 43, and the spring 44 are disposed so that radial direction positions where the sensor portions 42 and the ECT coils 43 come in contact with the heat-transfer-tube sealing portion 103 are different from each other.

As shown in FIGS. 2 and 3, the sensor portions 42 internally accommodate the ECT coils 43 and are also pressed against the heat-transfer-tube sealing portion 103. The sensor portions 42 are disposed so as to be movable in directions inclined at a predetermined angle with respect to a center axis L of the probe main unit 41. More specifically, the sensor portions 42 are disposed so as to be movable in directions inclined away from the center axis L toward the probe stabilizer 5 from the casing 2. Inclination angles $\alpha$ are determined on the basis of contact positions between the sensor portions 42 and the heat-transfer-tube sealing portion 103 and are angles that extend in the directions of the normals to the surfaces at the contact positions between the sensor portions 42 and the heat-transfer-tube sealing portion 103. Specifically, in the case in which the sensor portions 42 are brought into contact with an outer circumferential side of the heat-transfer-tube sealing portion 103, the inclination angles $\alpha$ increase, and, in the case in which they are brought into contact with an inner circumferential side thereof, the inclination angles $\alpha$ decrease.

As shown in FIG. 3, the sensor portions 42 are cylindrically formed members that are closed at one end. Outer surfaces at the closed ends are also contact surfaces 42A that are pressed against the heat-transfer-tube sealing portion 103. The contact surfaces 42A are formed in shapes that match the external shape of the heat-transfer-tube sealing portion 103 to be pressed against.

Gaps are formed between the sensor portions 42 and the probe main unit 41, and the sensor portions 42 can be moved slightly in the radial direction of the cylinders of the sensor portions 42, that is, in a perpendicular direction with respect to the movable directions of the sensor portions 42.

Furthermore, step portions 42B where the springs 44 are pressed against are provided on the outer circumferential sides of the sensor portions 42. The step portions 42B are steps whose diameters increase toward the heat-transfer-tube sealing portion 103 (downward in FIG. 3) from the probe main unit 41. The step portions 42B are formed at positions away from the contact surfaces 42A by predetermined distances. The predetermined distances are distances at which the springs 44 to be pressed against the step portions 42B do not influence the inspection for the presence/absence of defects in the heat-transfer-tube sealing portion 103.

In consideration of the influence on the detection of the presence/absence of defects by the ECT coils 43 with the eddy-current flaw detection method, the sensor portions 42 are formed of a material that is less likely to cause such an influence, such as plastic, etc.

The ECT coils 43 perform inspection for the presence/absence of defects in the heat-transfer-tube sealing portion 103. Specifically, the ECT coils 43 generate eddy currents in the heat-transfer-tube sealing portion 103 and detect the eddy currents generated in the heat-transfer-tube sealing portion 103. The ECT coils 43 are disposed close to the contact surfaces 42A of the sensor portions 42 and are pressed against the heat-transfer-tube sealing portion 103 along with the sensor portions 42.

With regard to the type of the ECT coils 43, a known type applied to the eddy-current flaw detection method can be employed; it is not particularly limited.

The springs 44 press the sensor portions 42 and the ECT coils 43 toward the heat-transfer-tube sealing portion 103. The springs 44 are disposed between the sensor portions 42 and the probe main unit 41 and are disposed so as to come in contact with the step portions 42B of the sensor portions 42. By making the springs 44 come in contact with the step portions 42B, the springs 44 and the ECT coils 43 are separated by the predetermined distances.

A known spring can be employed as the springs 44; it is not particularly limited.

As shown in FIG. 2, the probe stabilizer 5 is disposed at a distal end of the probe main unit 41 and prevents or suppresses misalignment between the probe main unit 41 and the heat-transfer tube 101.

The probe stabilizer 5 is mainly provided with a shaft portion 51, a contact portion 52, and bearing portions 53.

The shaft portion 51 is a member formed like a circular column and is attached to the distal end of the circular-column portion 41A in the probe main unit 41. Furthermore, it supports the contact portion 52 in a manner allowing rotation thereof via the bearing portions 53.

A pair of the bearing portions 53 are disposed at outer circumferential surfaces of the shaft portion 51.

The contact portion 52 is a member formed like a circular column and comes in contact with an inner circumferential surface of the heat-transfer tube 101. Furthermore, the shaft portion 51 is disposed at the inner side of the contact portion 52, and the bearing portions 53 are disposed between the shaft portion 51 and the contact portion 52.

Protruding portions 52A, which are formed in a ring shape and are also formed so as to protrude radially outward, are provided at outer circumferential surfaces at both ends of the contact portion 52. The contact portion 52 comes in contact with the heat-transfer tube 101 at radially outer ends of the protruding portions 52A.

As the material for forming the contact portion 52, an elastic material such as plastic is preferable. Elastic deformation of the contact portion 52 makes it possible for the heat-transfer tube 101 and the protruding portions 52A to reliably come in contact with each other.

The bearing portions 53 are disposed between the shaft portion 51 and the contact portion 52 and allow the shaft portion 51 and the contact portion 52 to relatively rotate about the center axis L. Specifically, the bearing portions 53 are disposed between the contact portion 52, when it is stationary by being in contact with the heat-transfer tube 101, and the shaft portion 51 that is attached to the probe main unit 41 and that rotates about the center axis L.

In this embodiment, the bearing portions 53, which are a pair of radial bearings, are disposed with a distance therebetween in a direction along the center axis L.

The securing portions 6 secure the inspection device 1 to the heat-transfer tubes 101 and the tube plate 102 and suppress the occurrence of misalignment of the probe main unit 41 and the heat-transfer tube 101 or, even if it occurs, reduce the extent of the misalignment. This embodiment will be described as applied to an example in which two securing portions 6 are provided in the casing.

As shown in FIG. 1, the securing portions 6 are mainly provided with securing shafts 61 and securing stabilizers (holding portions) 62.

The securing shafts 61 are columnar members that connect the casing 2 and the securing stabilizers 62.

The securing stabilizers 62 are disposed at distal ends of the securing shafts 61 and prevent or suppress misalignment between the probe main unit 41 and the heat-transfer tube 101. Because the specific configuration of the securing stabilizers 62 is similar to the configuration of the probe stabilizer 5, a description thereof will be omitted.

Next, inspection for the presence/absence of defects in the heat-transfer-tube sealing portions 103 with the inspection device 1 having the above-described configuration will be described.

As shown in FIGS. 1 and 2, when performing inspection for the presence/absence of defects in the heat-transfer-tube sealing portions 103, the probe portion 4 and the probe stabilizer 5 of the inspection device 1 are inserted into the same heat-transfer tube 101, and the two securing portions 6 are individually inserted into corresponding heat-transfer tubes 101.

As shown in FIG. 2, the probe portion 4 is inserted into the heat-transfer tube 101 until the flange portion 41B of the probe main unit 41 abuts against the tube plate 102.

On the other hand, the probe stabilizer 5 and the securing stabilizers 62 of the securing portions 6 come in contact with the inner circumferential surfaces of the heat-transfer tubes 101. Specifically, the protruding portions 52A of the contact portions 52 in the probe stabilizer 5 and the securing stabilizers 62 come in contact with the inner circumferential surfaces of the heat-transfer tubes 101. At this time, the protruding portions 52A are pressed against the inner circumferential surfaces of the heat-transfer tubes 101 due to the elastic deformation of the contact portions 52.

As shown in FIGS. 2 and 3, when the probe main unit 41 is pressed against the tube plate 102, the sensor portions 42 are pressed against the heat-transfer-tube sealing portion 103 by the springs 44. The sensor portions 42 come in contact with the heat-transfer-tube sealing portion 103 at the contact surfaces 42A.

In this state, inspection for the presence/absence of defects in the heat-transfer-sealing portion 103 is performed with the eddy-current flaw detection method. Specifically, eddy currents are formed in the heat-transfer-tube sealing portion 103 with the ECT coils 43, and the states of the eddy currents are detected by the ECT coils 43. If a defect, such as a blowhole, etc., exists in the heat-transfer-tube sealing portion 103, the above-described states of the eddy currents change as compared with the case in which the defect is absent. These changes are detected by the ECT coils 43.

A known method can be employed as the eddy-current flaw detection method used in this embodiment; it is not particularly limited.

Furthermore, when performing inspection for the presence/absence of defects in the heat-transfer-sealing portion 103 the probe portion 4 is rotationally driven by the rotation motor 3 first in one rotation direction and is then rotationally driven in the other rotation direction. When the probe portion 4 is rotationally driven, the sensor portions 42 pressed against the heat-transfer-tube sealing portion 103 are also rotationally driven, and the presence/absence of defects in the heat-transfer-tube sealing portion 103 is inspected by the ECT coils 43.

As this time, if misalignment occurs between the probe main unit 41 and the heat-transfer tube 101, the sensor portions 42 move so that the contact surfaces 42A come in close contact with the heat-transfer-tube sealing portion 103, in other words, to positions in the heat-transfer-tube sealing portion 103 that match with the external shapes of the contact surfaces 42A.

As shown in FIG. 4, the three ECT coils 43 come in contact with the heat-transfer-tube sealing portion 103 at different positions. Defining the one disposed at the radially innermost side as an inner coil 43N, the one disposed at the radially outer-most side as an outer coil 43F, and the one disposed between the two as a middle coil 43M, a region inspected by the inner coil 43N and a region inspected by the middle coil 43M overlap with each other. In addition, the region inspected by the middle coil 43M and a region inspected by the outer coil 43F overlap with each other.

For example, in the case in which the diameters of the inner coil 43N, the middle coil 43M, and the outer coil 43F are about 3 mm, it is preferable that the centers of these coils be shifted in the radial directions within a range of about 0 mm to about 3 mm, and, in addition, it is more preferable that they be shifted by about 1 mm.

Furthermore, inspection for the presence/absence of defects is sequentially performed by the three ECT coils 43. Specifically, when the inner coil 43N is performing inspection for the presence/absence of defects, the middle coil 43M and the outer coil 43F are not performing inspection for the presence/absence of defects. Similarly, when the middle coil 43M is performing inspection, the inner coil 43N and the outer coil 43F are not performing inspection. When the outer coil 43F is performing inspection, the inner coil 43N and the middle coil 43M are not performing inspection.

This switching may be done at any timing so long as the timing allows inspection for the presence/absence of defects; it is not particularly limited.

When inspection of the heat-transfer-tube sealing portion 103 is completed at one heat-transfer tube 101, as described above, the probe portion 4 is pulled out from the one heat-transfer tube 101, the probe portion 4 is inserted into the next heat-transfer tube 101, and an inspection is performed for a heat-transfer-tube sealing portion 103 of the next heat-transfer tube 101. By repeating such a process, inspection is performed for the heat-transfer-tube sealing portions 103 of all of the heat-transfer tubes 101.

Next, inspection results for when the probe portion 4 is rotationally driven in one rotation direction and the other rotation direction will be described.

Figure 5A:
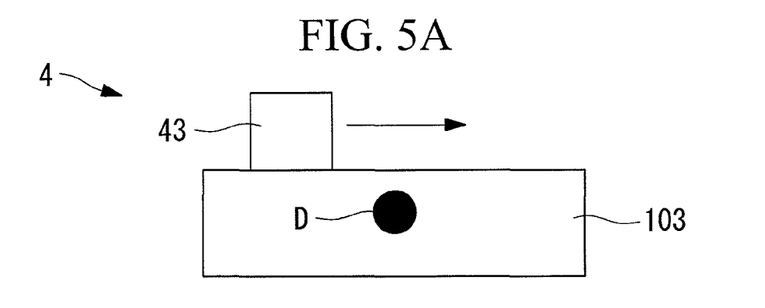
FIG. 5A is a schematic diagram for explaining inspection results for when the probe portion is rotationally driven in one rotation direction.
Figure 5B:
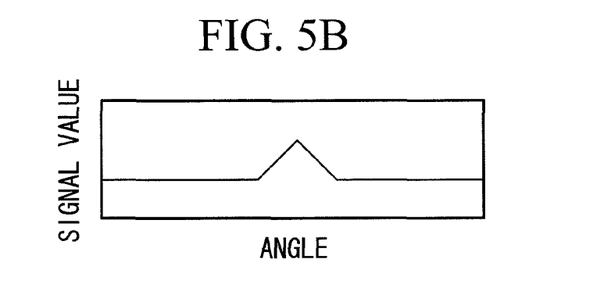
FIG. 5B is a schematic diagram for explaining the inspection results for when the probe portion is rotationally driven in one rotation direction.
Figure 6A:
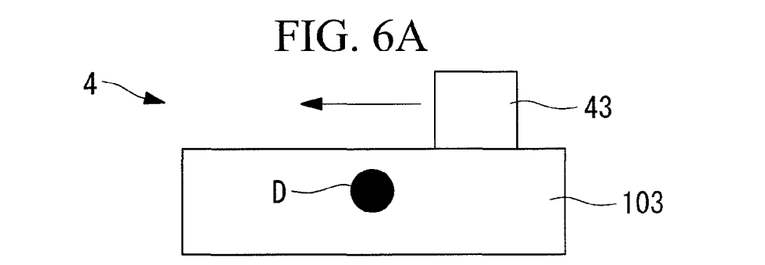
FIG. 6A is a schematic diagram for explaining inspection results for when the probe portion is rotationally driven in the other rotation direction.
Figure 6B:
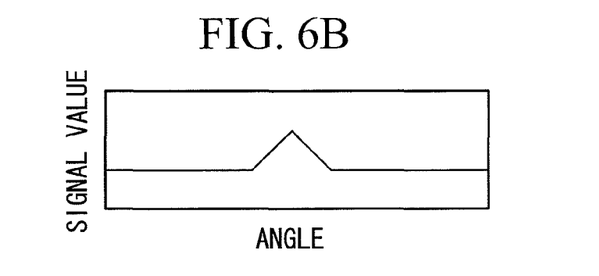
FIG. 6B is a schematic diagram for explaining the inspection results for when the probe portion is rotationally driven in the other rotation direction.

FIGS. 5A and 5B are schematic diagrams for explaining inspection results for when the probe portion is rotationally driven in one rotation direction. FIGS. 6A and 6B are schematic diagrams for explaining inspection results for when the probe portion is rotationally driven in the other rotation direction.

First, the case in which a defect D exists in the heat-transfer-tube sealing portion 103 will be described.

As shown in FIG. 5A, when the probe portion 4 is rotationally driven in one rotation direction, the ECT coil 43 is also moved in one rotation direction (right direction in FIG. 5A). The consequently obtained inspection result is the change in signal value shown in FIG. 5B. That is, the signal value changes at an angle where the defect D exists.

As shown in FIG. 6A, on the other hand, when the probe portion 4 is rotationally driven in the other rotation direction, the ECT coil 43 is moved in the other rotation direction (left direction in FIG. 6A). The consequently obtained inspection result is the change in signal value shown in FIG. 6B. That is, as with the case in which the probe portion 4 is rotationally driven in one rotation direction, the signal value changes at the angle where the defect D exists.

In other words, in the case in which the defect D exists in the heat-transfer-tube sealing portion 103, substantially similar inspection results are obtained when the probe portion 4 is rotationally driven in one rotation direction and the other rotation direction.

Next, the case in which a protruding portion ND exists at the surface of the heat-transfer-tube sealing portion 103 and the defect D does not exist will be described.

Figure 7A:
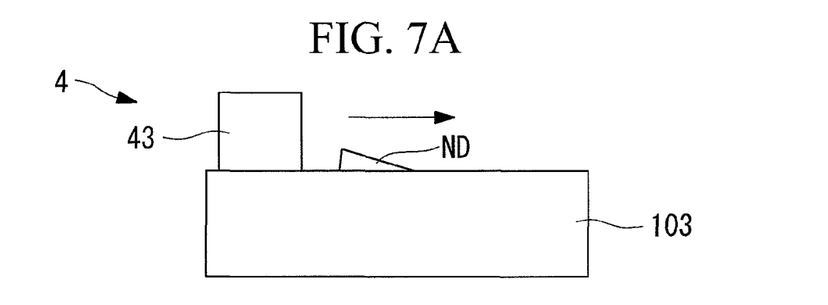
FIG. 7A is a schematic diagram for explaining inspection results for when the probe portion is rotationally driven in one direction.
Figure 7B:
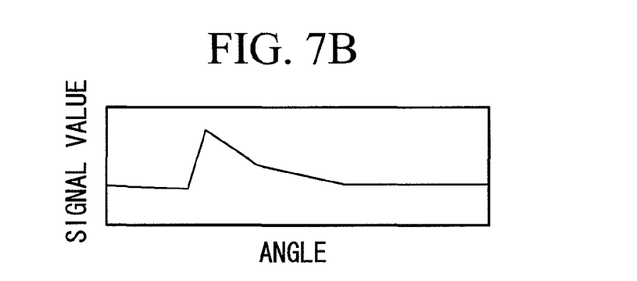
FIG. 7B is a schematic diagram for explaining the inspection results for when the probe portion is rotationally driven in one direction.
Figure 8A:
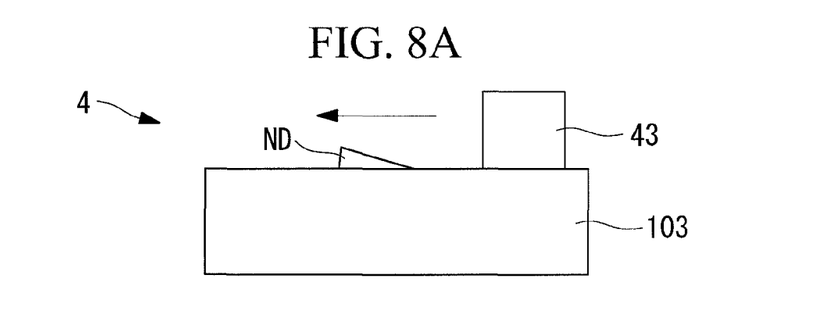
FIG. 8A is a schematic diagram for explaining inspection results for when the probe portion is rotationally driven in the other rotation direction.
Figure 8B:
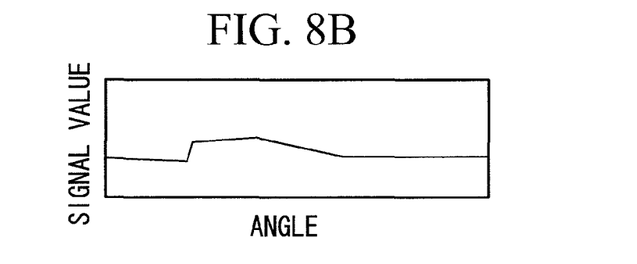
FIG. 8B is a schematic diagram for explaining the inspection results for when the probe portion is rotationally driven in the other rotation direction.

FIGS. 7A and 7B are schematic diagrams for explaining inspection results for when the probe portion is rotationally driven in one rotation direction. FIGS. 8A and 8B are schematic diagrams for explaining inspection results for when the probe portion is rotationally driven in the other rotation direction.

Here, the protruding portion ND has an inclined surface with a large slope when the probe portion 4 moves in one rotation direction and has an inclined surface with a small slope when the probe portion 4 moves in the other rotation direction.

As shown in FIG. 7A, when the probe portion 4 is rotationally driven in one rotation direction, the ECT coil 43 is also moved in one rotation direction (right direction in FIG. 7A). The consequently obtained inspection result is the change in signal value shown in FIG. 7B. That is, the signal value abruptly increases at the point when the ECT coil 43 reaches the protruding portion ND, and then, the signal value gradually decreases.

As shown in FIG. 8A, on the other hand, when the probe portion 4 is rotationally driven in the other rotation direction, the ECT coil 43 is moved in the other rotation direction (left direction in FIG. 8A). The consequently obtained inspection result is the change in signal value shown in FIG. 8B. That is, the signal value gradually increases from the point when the ECT coil 43 reaches the protruding portion ND, and the maximum signal value is considerably reduced as compared with the case in which the probe portion 4 is rotationally driven in one rotation direction.

In other words, in the case in which the defect D does not exist and only the protruding portion ND exists at the heat-transfer-tube sealing portion 103, the inspection result obtained by rotationally driving the probe portion 4 in one rotation direction considerably differs from the inspection result obtained by rotationally driving it in the other rotation direction.

Next, detection signals detected by the ECT coils 43 will be described.

Figure 9A:
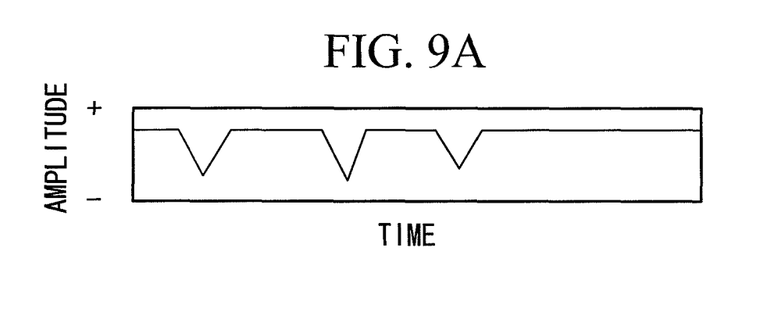
FIG. 9A is a graph showing amplitudes of signal values detected by an outer coil, showing real-part amplitudes.
Figure 9B:
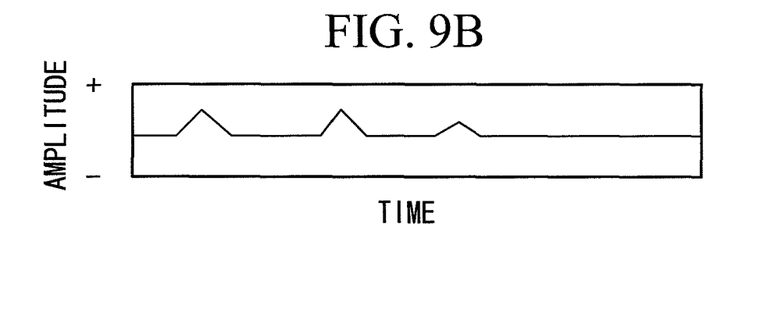
FIG. 9B is a graph showing amplitudes of the signal values detected by the outer coil, showing imaginary-part amplitudes.
Figure 10A:
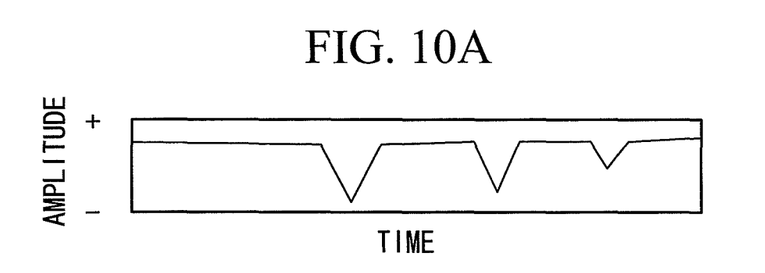
FIG. 10A is a graph showing amplitudes of signal values detected by a middle coil, showing real-part amplitudes.
Figure 10B:
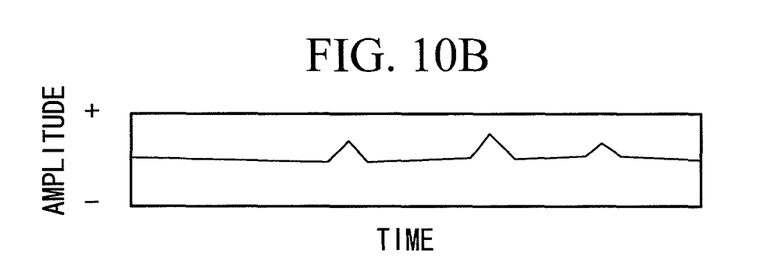
FIG. 10B is a graph showing amplitudes of the signal values detected by the middle coil, showing imaginary-part amplitudes.
Figure 11A:
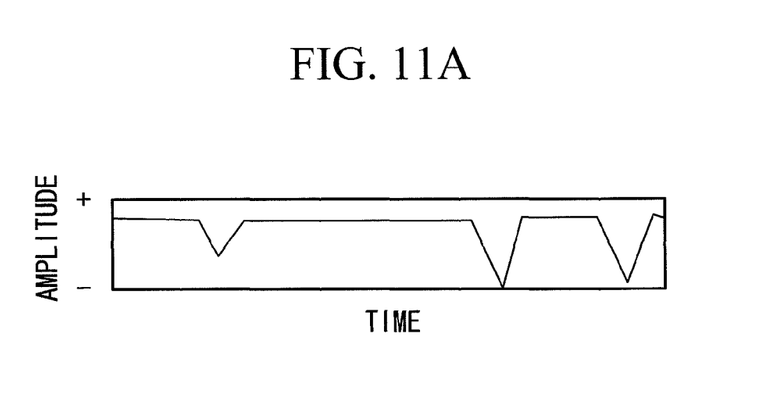
FIG. 11A is a graph showing amplitudes of signal values detected by an inner coil, showing real-part amplitudes.
Figure 11B:
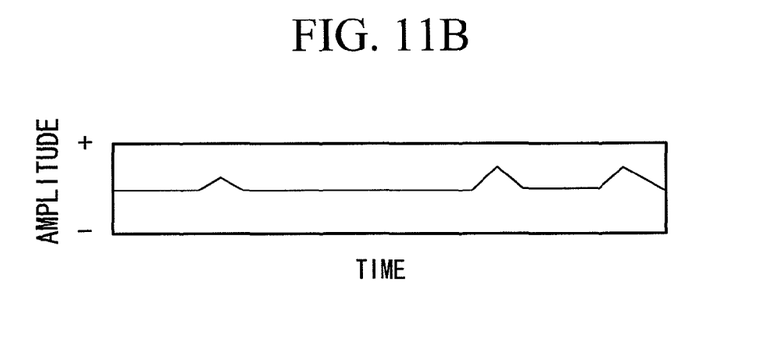
FIG. 11B is a graph showing amplitudes of the signal values detected by the inner coil, showing imaginary-part amplitudes.

FIG. 9A is a graph showing amplitudes of signal values detected by the outer coil, showing real-part amplitudes. FIG. 9B is a graph showing amplitudes of signal values detected by the outer coil, showing imaginary-part amplitudes. FIG. 10A is a graph showing amplitudes of signal values detected by the middle coil, showing real-part amplitudes. FIG. 10B is a graph showing amplitudes of signal values detected by the middle coil, showing imaginary-part amplitudes. FIG. 11A is a graph showing amplitudes of signal values detected by the inner coil, showing real-part amplitudes. FIG. 11B is a graph showing amplitudes of signal values detected by the inner coil, showing imaginary-part amplitudes.

In FIGS. 9A to 11B, the horizontal axis shows the elapsed time since the inspection started. The circumferential-direction angle at the heat-transfer-tube sealing portion 103 is a function of the above-described elapsed time.

On the other hand, the vertical axis shows the real part or the imaginary part of the detected signals, as described above, and the amplitude is zero at the center on the vertical axis.

Examining the signals values detected by the outer coil 43F, as shown in FIGS. 9A and 9B, both the real-part amplitudes and the imaginary-part amplitudes change at portions where defects exist, and the amplitudes change in opposite directions. The patterns are similar for the middle coil 43M and the inner coil 43N (see FIGS. 10A, 10B, 11A, and 11B).

Figure 12:
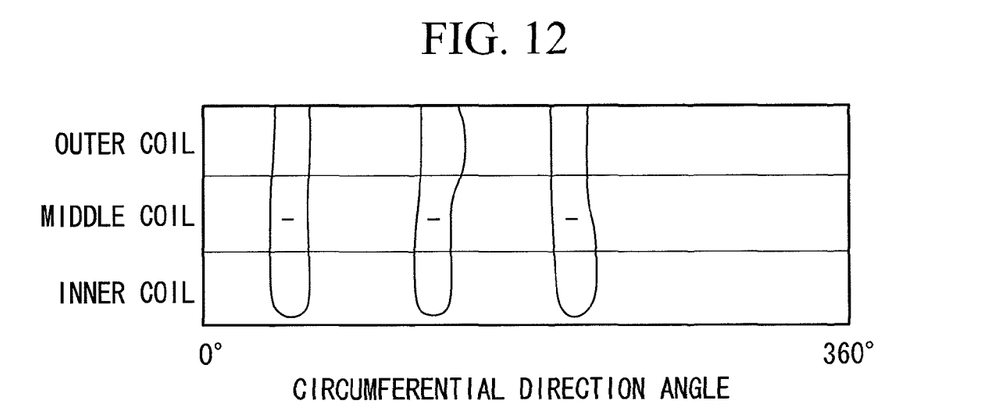
FIG. 12 is a band-shaped graph showing changes in signal values detected by the outer coil, the middle coil, and the inner coil.
Figure 13:
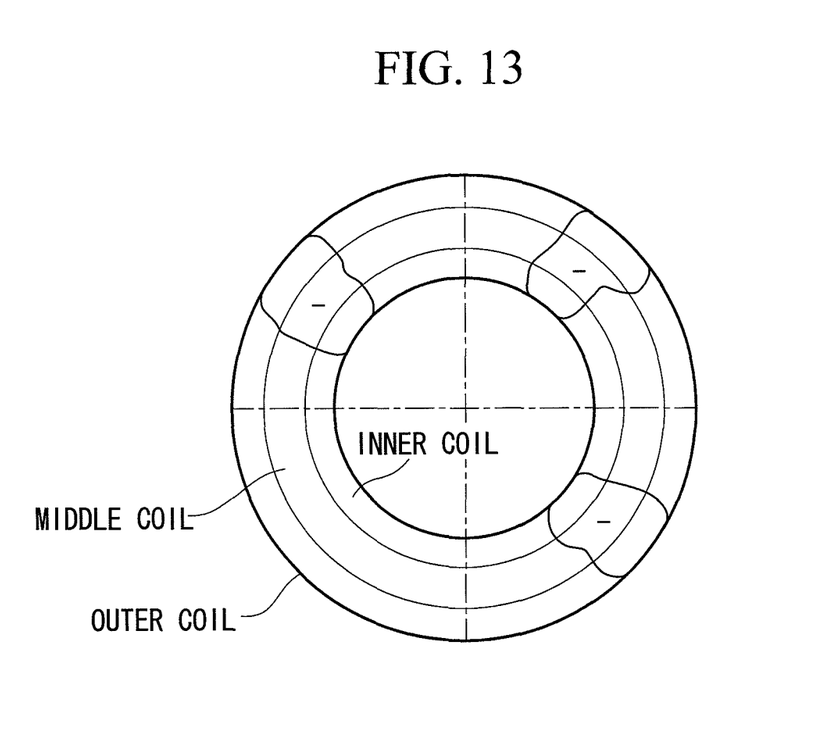
FIG. 13 is a ring-shaped graph showing changes in the signal values detected by the outer coil, the middle coil, and the inner coil.

FIG. 12 is a band-shaped graph that shows the changes in the signal values detected by the outer coil, the middle coil, and the inner coil. FIG. 13 is a ring-shaped graph that shows the changes in the signal values detected by the outer coil, the middle coil, and the inner coil.

FIG. 12 shows the changes in the real-part amplitudes of the signal values detected by the outer coil 43F, the middle coil 43M, and the inner coil 43N. The horizontal axis shows the circumferential-direction angle at the heat-transfer-tube sealing portion 103.

By doing so, the positions at which defects occur in the heat-transfer-tube sealing portion 103 can easily be ascertained.

FIG. 13 additionally shows the changes in the real-part amplitudes of the signals values detected by the outer coil 43F, the middle coil 43M, and the inner coil 43N in such a manner as to match the shape of the heat-transfer-tube sealing portion 103.

By doing so, the positions at which defects occur in the heat-transfer-tube sealing portion 103 can be ascertained more easily.

With the above-described configuration, the probe main unit 41 is inserted into the tube, and the flange portion 41B is pressed against the tube plate 102, and thereby, the sensor portions 42 are pressed against the heat-transfer-tube sealing portion 103. By rotating the probe main unit 41 with respect to the heat-transfer-tube 101 in this state, the sensor portions 42 can be moved in the circumferential direction at the surface of the heat-transfer-tube sealing portion 103, and inspection for the presence/absence of defects at the heat-transfer-tube sealing portion 103 can be performed. In other words, it is possible to stably perform inspection for the presence/absence of defects in predetermined areas of the plurality of the heat-transfer-tube sealing portions 103, and it is possible to perform inspection for the presence/absence of defects at the plurality of the heat-transfer-tube sealing portions 103 in a short period of time. Accordingly, all of the heat-transfer-tube sealing portions in a steam generator can be inspected. Because the inspection is by the eddy-current flaw detection method, it is also possible to analyze defect shapes on the basis of the inspection results.

Because the probe main unit 41 can be rotated in both directions, by comparing the inspection results obtained from one rotation direction and the inspection results obtained from the other rotation direction, disturbance noise due to surface protrusions, etc. can be removed from the inspection results.

The rotation direction of the probe main unit 41 with respect to the heat-transfer tube 101 may be both directions or may be only one direction, that is, one rotation direction or the other rotation direction; it is not particularly limited.

The sensor portions 42 are pressed against the heat-transfer-tube sealing portion 103 by the springs 44 which are elastic members made of metal. Because of this, as compared with the case in which elastic members formed of other materials are employed, the sensor portions 42 can be more reliably pressed against the heat-transfer-tube sealing portion 103.

Furthermore, because the springs 44 made of metal, which affect the inspection results of the eddy-current flaw detection method regarding the presence/absence of defects, are disposed away from the ECT coils 43 of the sensor portions 42, the presence/absence of defects at the heat-transfer-tube sealing portion 103 can be accurately inspected.

Because the sensor portions 42 are pressed against the heat-transfer-tube sealing portion 103 at positions separated in the circumferential direction at equal intervals, the center axis (center) of the probe main unit 41 is aligned with the center axis (center) of the heat-transfer tube 101. Accordingly, the distances between the sensor portions 42 and the heat-transfer-tube sealing portion 103 are easy to keep constant, and disturbance noise due to fluctuations of these distances are less likely to be included in the inspection results by the sensor portions 42.

By fully rotating the probe main unit 41 with respect to the heat-transfer tube 101, a greater area at the heat-transfer-tube sealing portion 103 can be inspected for the presence/absence of defects as compared with the case in which one sensor portion 42 is provided. Specifically, by sequentially arranging the plurality of the sensor portions 42 from outside to inside in the radial direction of the heat-transfer-tube sealing portion 103, a greater area at the heat-transfer-tube sealing portion 103 can be inspected in a short period of time.

Furthermore, the plurality of the sensor portions 42 may be disposed so that the inspection areas of the individual sensor portions 42 do not overlap with each other or they may be arranged so that a portion of the region inspected by one sensor portion 42 overlaps with the region inspected by another adjacent sensor portion 42.

In the case in which the plurality of the sensor portions 42 are disposed so that an overlap occurs, one defect can be detected by at least two sensor portions 42, making it possible to remove disturbance noise from the detection results from the sensor portions 42. Specifically, the probability that the plurality of the sensor portions 42 cause disturbance noise to occur at the same position is low, and thus, in many cases, the disturbance noise appears in the detection result from one sensor portion 42. On the other hand, the defect is detected at the same position by the plurality of the sensor portions 42. Accordingly, the disturbance noise can easily be removed from the detection results from the sensor portions 42.

Because inspection by the other sensor portions 42 is not performed when the one sensor portion 42 is performing the inspection for the presence/absence of defects, it is possible to prevent the other sensor portions 42 from affecting the inspection result from the one sensor portion 42. Furthermore, because inspection is sequentially performed by the plurality of the sensor portions 42, for example, the inspection region at the heat-transfer-tube sealing portion 103 can be inspected without a gap while the probe main unit 41 fully rotates.

Even if misalignment occurs, in which the center axis of the probe main unit 41 and the center axis of the heat-transfer tube 101 are shifted, the sensor portions 42 easily move to the regions of the heat-transfer-tube sealing portion 103 that have the same shapes as the heat-transfer-tube sealing portion 103 and the contact surfaces 42A. In other words, the tracking performance is high. As a result, the precision of the inspection results from the sensor portions 42 for the presence/absence of defects can be increased.

Because the center axis of the probe main unit 41 is aligned with the center axis of the heat-transfer tube 101 with the probe stabilizer 5, even though inspection for the presence/absence of defects at the heat-transfer-tube sealing portion 103 is performed by rotating the probe main unit 41, fluctuations in the distances between the sensor portions 42 and the heat-transfer-tube sealing portion 103 can be suppressed. As a result, the precision of the inspection results from the sensor portions 42 for the presence/absence of defects can be increased.

The securing stabilizers 62 and the probe stabilizer 5 are individually inserted into the heat-transfer tubes 101 and come in contact with the inner circumferential surfaces thereof, thereby facilitating alignment of the center axis of the probe main unit 41 with the center axis of the of the heat-transfer tube 101.

Furthermore, as compared with the case in which only the probe stabilizer 5 and the probe main unit 41 are inserted into the heat-transfer tube 101, because the securing stabilizers 62 are inserted into the other heat-transfer tubes 101, the inspection device 1 is secured to the heat-transfer tubes 101 and the tube plate 102 with the probe stabilizer 5 and the securing stabilizers 62. Because of this, even though the probe main unit 41 is rotated with respect to the heat-transfer tube 101, recoil therefrom does not cause the inspection device 1 to change its orientation or to be moved. That is, even though the probe main unit 41 and the sensor portions 42 are rotated, the occurrence of misalignment in the probe main unit 41 can be prevented.

The technical scope of the present invention is not limited to the above-described embodiment, and various alterations can be added within a range that does not depart from the spirit of the present invention.

For example, although the present invention is described in the above-described embodiment as applied to an inspection device employed in defect inspection for heat-transfer-tube sealing portions in an SG, the present invention can be applied to inspection devices that perform defect inspection for non-magnetic metal materials, and there is no particular limitation.

REFERENCE SIGNS LIST 1 inspection device
5 probe stabilizer (aligning portion)
41 probe main unit (main unit)
42 sensor portion (probe)
44 spring (pressing portion)
62 securing stabilizer (holding portion)
101 heat-transfer tube (tube)
102 tube plate
103 heat-transfer-tube sealing portion (welded portion)

The invention claimed is:

1. An inspection device that employs an eddy-current flaw detection method to perform inspection for a presence or an absence of a defect in a welded portion between a tube and a tube plate, the inspection device comprising:

a main unit that has a circular-column portion, which is inserted into the tube, and a flange portion, which is connected to the circular-clumn portion and which is pressed against the tube plate, and that is rotatable with respect to the welded portion;

a probe that is disposed at a connecting portion between the circular-column portion and the flange portion inside the main unit, that can be moved close to and away from the welded portion, and that detects a defect in the welded portion;

a pressing portion that presses the probe toward the welded portion; and an aligning portion that is provided at a distal end of the circular-column portion, that comes in contact with an inner circumferential surface of the tube, and that aligns a center of the main unit and a center of the tube.

2. An inspection device according to claim 1, wherein the pressing portion is an elastic member, and the pressing portion is disposed at least a predetermined distance away from the probe.

3. An inspection device according to claim 1, wherein the main unit is provided with a plurality of the probes, and the plurality of the probes are disposed in a circumferential direction of the main unit at equal intervals.

4. An inspection device according to claim 1, wherein the main unit is provided with a plurality of the probes, and each of the plurality of the probes is pressed against the welded portion at a different radial position.

5. An inspection device according to claim 3, wherein the plurality of the probes sequentially perform inspection for the presence or the absence of a defect in the welded portion.

6. An inspection device according to claim 1, wherein a surface of the probe that comes in contact with the welded portion is formed so as to match a shape of the welded portion with which the probe is made to come in contact.

7. An inspection device according to claim 1, further comprising a holding portion that is inserted into another tube other than the tube into which the circular-column portion is inserted and that comes in contact with an inner circumferential surface of the other tube.

8. An inspection device according to claim 1, wherein, the aligning portion includes a contact portion that is a cylindrical member and that contacts with an inner circumferential surface of the tube;

a shaft portion that is attached to the distal end of the circular-column portion in the main unit and that is disposed at the inner side of the contact portion; and bearing portions that are disposed between the shaft portion and the contact portion.

9. An inspection device according to claim 8, wherein, the contact portion includes protruding portions that are formed in a ring shape and that are formed so as to protrude radially outward, and that are provided at outer circumferential surfaces at both ends of the contact portion.

10. An inspection device according to claim 9, wherein the contact portion is made of an elastic material.

* * * * *